United States Patent [19]

Yoshida

[11] Patent Number: 4,916,253
[45] Date of Patent: Apr. 10, 1990

[54] FLUOROBENZOATES AND PROCESS FOR THEIR PRODUCTION

[75] Inventor: Yasuo Yoshida, Ihara, Japan

[73] Assignee: Ihara Chemical Industry Company, Ltd., Tokyo, Japan

[21] Appl. No.: 207,230

[22] Filed: Jun. 16, 1988

[30] Foreign Application Priority Data

Jun. 22, 1987 [JP] Japan ................................ 62-155039

[51] Int. Cl.$^4$ .............................................. C07C 69/76
[52] U.S. Cl. ................................................... 560/103
[58] Field of Search ......................................... 170/103

[56] References Cited

FOREIGN PATENT DOCUMENTS 0259048  9/1988  European Pat. Off. .
05487   11/1986  Int'l Pat. Institute .
126460   2/1982  Japan .

OTHER PUBLICATIONS

Chemical Abstracts, vol. 66, 94742j, 1967.

*Primary Examiner*—Paul J. Killos
*Attorney, Agent, or Firm*—Oblon, Spivak, McClelland, Maier & Neustadt

[57] ABSTRACT

A fluorobenzoate having the formula:

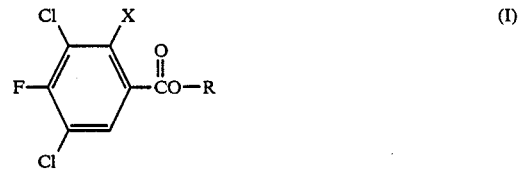

wherein X is a fluorine atom or a hydrogen atom, and R is an alkyl group.

3 Claims, No Drawings

FLUOROBENZOATES AND PROCESS FOR THEIR PRODUCTION

The present invention relates to novel fluorobenzoates and a process for their production.

In recent years, an attention has been drawn to fluorine-containing agricultural chemicals and medicines as they have excellent pharmacological or physiological activities. They have been positively studied. For example, fluorine-containing urea insecticides and fluorine-containing quinolone germicides have been proposed. Among them, N-(3,5-dichloro-2,4-difluorophenyl)-N'-(2,6-difluorobenzoyl)urea disclosed in Japanese Unexamined Patent Publication No. 126460/1982 is known to have high activities as an insecticide. Further, as a method for its production, it is known to react 3,5-dichloro-2,4-difluorophenyl isocyanate with 2,6-difluorobenzamide.

The fluorophenyl isocyanate used in the method disclosed in the above publication is prepared usually by reacting the corresponding aniline with phosgene. However, phosgene is a poisonous gas, and its use is restricted by regulations. Under the circumstances, it has been desired to develop a method for producing the phenyl isocyanate without using phosgene. As a method for producing an isocyanate without using phosgene, it has been recently proposed to fluorinate 2,3,4,5-tetrachlorobenzoyl chloride to obtain 3,5-dichloro-2,4-difluorobenzoyl fluoride, which is reacted with sodium azide to obtain the corresponding benzoyl azide, which is then heated to obtain 3,5-dichloro-2,4-difluorophenyl isocyanate (International Patent Application published under WO86/05487). However, this method employs explosive sodium azide, and is therefore not satisfactory for practical industrial application.

Under these circumstances, the present inventors have conducted extensive researches to develop a method for producing a fluorophenyl isocyanate in a different manner on an industrial scale. As a result, it has been found that when the corresponding chlorobenzoate is reacted with a metal fluoride in the presence of a certain specific catalyst in a certain specific solvent or in the absence of a solvent, a novel fluorobenzoate can be produced while suppressing a side reaction of the ester group, and further that the above-mentioned fluorophenyl isocyanate can be produced from this fluorobenzoate. The present invention has been accomplished on the basis of these discoveries.

The present invention provides a fluorobenzoate having the formula:

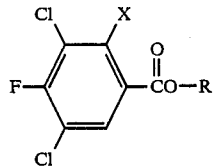

(I)

wherein X is a fluorine atom or a hydrogen atom, and R is an alkyl group, which is useful as an intermediate for the production of fluorine-containing urea insecticides or fluorine-containing quinolone germicides.

Further, the present invention provides a process for producing a fluorobenzoate of the formula I, which comprises reacting a chlorobenzoate having the formula:

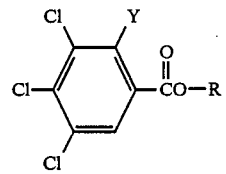

(II)

wherein Y is a hydrogen atom or a chlorine atom, and R is as defined above, with a metal fluoride. The reaction is conducted either in an aprotic polar solvent in the presence of at least one salt selected from the group consisting of quaternary phosphonium salts, quaternary ammonium salts and pyridinium salts, as catalyst, or in the presence of a combination of at least one salt selected from the group consisting of quaternary phosphonium salts, quaternary ammonium salts and pyridinium salts, and at least one compound selected from the group consisting of crown ethers and polyalkylene glycols, as catalyst.

Now, the present invention will be described in detail with reference to the preferred embodiments.

The fluorobenzoate of the present invention is a compound of the formula I wherein X is a hydrogen atom or a fluorine atom, and R is an alkyl group, preferably a $C_1$–$C_5$ alkyl group such as a methyl group, an ethyl group, a propyl group, an isopropyl group, a t-butyl group, a sec-butyl group or a neopentyl group. Such a fluorobenzoate includes, for example, methyl 3,5-dichloro-4-fluorobenzoate, ethyl 3,5-dichloro-4-fluorobenzoate, isopropyl 3,5-dichloro-4-fluorobenzoate, t-butyl 3,5-dichloro-4-fluorobenzoate, sec-butyl 3,5-dichloro-4-fluorobenzoate, neopentyl 3,5-dichloro-4-fluorobenzoate, methyl 3,5-dichloro-2,4-difluorobenzoate, ethyl 3,5-dichloro-2,4-difluorobenzoate, isopropyl 3,5-dichloro-2,4-difluorobenzoate, t-butyl 3,5-dichloro-2,4-difluorobenzoate, sec-butyl 3,5-dichloro-2,4-difluorobenzoate and neopentyl 3,5-dichloro-2,4-difluorobenzoate.

The chlorobenzoate used as a starting material in the process for the production of a fluorobenzoate of the present invention is a compound of the formula II wherein Y is a hydrogen atom or a chlorine atom, and R is an alkyl group, preferably a $C_1$–$C_5$ alkyl group such as a methyl group, an ethyl group, a propyl group, an isopropyl group, a t-butyl group, a sec-butyl group or a neopentyl group. Particularly preferred as R is a neopentyl group. Such a chlorobenzoate includes, for example, methyl 3,4,5-trichlorobenzoate, ethyl 3,4,5-trichlorobenzoate, isopropyl 3,4,5-trichlorobenzoate, t-butyl 3,4,5-trichlorobenzoate, sec-butyl 3,4,5-trichlorobenzoate, neopentyl 3,4,5-trichlorobenzoate, methyl 2,3,4,5-tetrachlorobenzoate, ethyl 2,3,4,5-tetrachlorobenzoate, isopropyl 2,3,4,5-tetrachlorobenzoate, t-butyl 2,3,4,5-tetrachlorobenzoate, sec-butyl 2,3,4,5-tetrachlorobenzoate and neopentyl 2,3,4,5-tetrachlorobenzoate.

The quaternary phosphonium salts, the quaternary ammonium salts and the pyridinium salts used as catalyst in the process of the present invention may be compounds represented by the following formulas III, IV and V, respectively.

(III)

(IV)

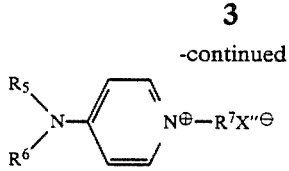
(V)

wherein each of $R^1$, $R^2$, $R^3$ and $R^4$ which may be the same or different is an alkyl group, an aryl group or an aralkyl group, X' is a halogen atom, each of $R^5$, $R^6$ and $R^7$ which may be the same or different is an alkyl group, and X" is a halogen atom.

Specific examples of such compounds include quaternary phosphonium salts such as tetraphenyl phosphonium bromide, tetraphenyl phosphonium chloride, benzyltributyl phosphonium chloride, benzyltriphenyl phosphonium chloride and triphenylmethyl phosphonium chloride; quaternary ammonium salts such as tetramethylammonium chloride, tetraethylammonium bromide, tetrabutylammonium bromide, tetrabutylammonium iodide, tetrahexylammonium bromide, tetraoctylammonium chloride, ethyltrimethylammonium chloride, butyltriethylammonium chloride, lauryltrimethylammonium bromide, ethyltributylammonium bromide, isobutyltributylammonium bromide, hexyltributylammonium bromide, octyltributylammonium bromide, lauryltributylammonium bromide, methyltrioctylammonium bromide, tetraphenylammonium chloride, benzyltrimethylammonium bromide, benzyltriethylammonium chloride, benzyltripropylammonium chloride, benzyltrihexylammonium chloride and benzyltrioctylammonium chloride; and pyridinium salts such as N-(2-ethylhexyl)-4-dimethylaminopyridinium chloride, N-(2-ethylhexyl)-4-di-n-butylaminopyridinium chloride, N-(2-ethylhexyl)-4-di-n-hexylaminopyridinium chloride, N-neopentyl-4-dimethylaminopyridinium chloride, N-neopentyl-4-di-n-butylaminopyridinium chloride, N-neopentyl-4-di-n-hexylaminopyridinium chloride, N-(2-ethylhexyl)-4-dimethylaminopyridinium chloride, N-(2-ethylhexyl)-4-di-n-butylaminopyridinium bromide, N-(2-ethylhexyl)-4-di-n-hexylaminopyridinium bromide, N-neopentyl-4-dimethylaminopyridinium bromide, N-neopentyl-4-di-n-butylaminopyridinium bromide and N-neopentyl-4-di-n-hexylaminopyridinium bromide.

Further, in the present invention, a combination of at least one salt selected from the group consisting of the above quaternary phosphonium salts, quaternary ammonium salts and pyridinium salts and at least one compound selected from the group consisting of crown ethers and polyalkylene glycols may be used as catalyst.

The crown ethers include, for example, 18-crown-6, dibenzo-18-crown-6, dicyclohexano-18-crown-6, 12-crown-4, 15-crown-5 and dibenzo-24-crown-8. Among them, 18-crown-6, dibenzo-18-crown-6 and dicyclohexano 18-crown-6 are particularly preferred.

As the polyalkylene glycols, compounds of the formula:

$$R^9O(R^8O)_zR^{10}$$ (V)

wherein $R^8$ is an alkylene group, each of $R^9$ and $R^{10}$ which may be the same or different is a hydrogen atom, an alkyl group, an aryl group or an aralkyl group, and z is an integer of at least 2 may be used. Such compounds include, for example, glycols such as diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol; monoalkyl ethers such as monomethyl, monoethyl, monopropyl and monobutyl ethers of such glycols; dialkyl ethers such as tetraethylene glycol dimethyl ether and pentaethylene glycol dimethyl ether; phenyl ethers; benzyl ethers; and polyalkylene glycols such as polyethylene glycol dimethyl ether (average molecular weight: 300), polyethylene glycol dibutyl ether (average molecular weight: 300) and polyethylene glycol dimethyl ether (average molecular weight: 400). Among them, compounds wherein both $R^9$ and $R^{10}$ are alkyl groups, aryl groups or aralkyl groups are preferred.

In the present invention, such crown ethers or such polyalkylene glycols may be used alone or in combination as a mixture of two or more. Further, such a crown ether and such a polyalkylene glycol may be used in combination.

In the present invention, the catalyst may be used usually in an amount within a range of from 1 to 50 mol %, preferably from 5 to 40 mol %, per mol of the chlorobenzoate of the formula II. When the crown ether or polyalkylene glycol and the quaternary phosphonium salt, quaternary ammonium salt or pyridinium salt are used in combination as the catalyst, the proportions of the two components are preferably such that the amount of the crown ether or polyalkylene glycol does not exceed 4 mol times of the amount of the quaternary phosphonium salt, quaternary ammonium salt or pyridinium salt. When the crown ether or polyalkylene glycol is used alone without the quaternary phosphonium salt, the desired fluorobenzoate does not substantially form.

The metal fluoride used in the process of the present invention may be, for example, potassium fluoride or cesium fluoride. Particularly preferred is spray-dried conducted under atmospheric pressure. The reaction time is usually from 1 to 20 hours.

As shown below, the novel fluorobenzoate obtained by the process of the present invention can be reacted with hydrazine by a conventional method to obtain the corresponding fluorobenzoyl hydrazide, which is further reacted with sodium nitrite to obtain the corresponding fluorobenzoyl azide, which is then heated to obtain the above-mentioned fluorophenyl isocyanate. Further, by reacting this fluorophenyl isocyanate with benzamide, it is possible to produce a fluorine-containing urea insecticide as disclosed in Japanese Unexamined Patent Publication No. 126460/1982.

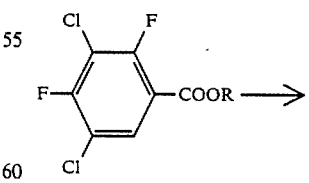

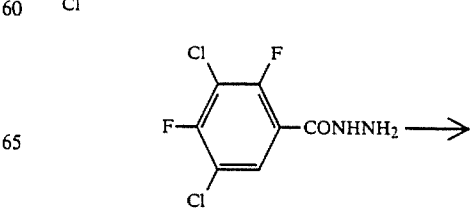

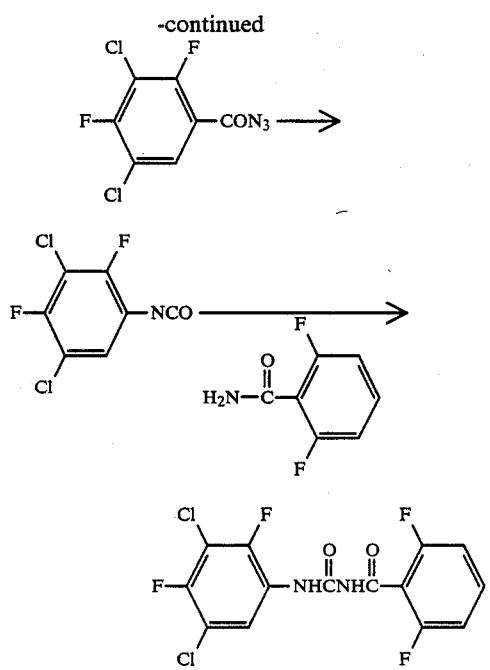

According to the process of the present invention, a chlorobenzoate of the formula II is reacted with a metal fluoride in the presence of the specific catalyst and the specific solvent, whereby it is possible to suppress side reactions such as transfer of the —OR group in the formula potassium fluoride. Such a metal fluoride is used preferably in an amount of from 1 to 2 times in equivalent to the chlorine atom to be substituted in the chlorobenzoate of the formula II.

This reaction is conducted usually in the presence of a solvent to facilitate the reaction, or may be conducted in the absence of a solvent. When a solvent is used, it is preferred to use an aprotic polar solvent such as sulfolane, dimethyl sulfone, 1,3-dimethylimidazolin-2-one, dimethylformamide, N-methylpyrrolidone, tetramethyl urea or dimethyl sulfoxide. When at least one salt selected from the group consisting of the above-mentioned quaternary phosphonium salts, quaternary ammonium salts and pyridinium salts is used alone as the catalyst, the reaction is preferably conducted in an aprotic polar solvent. This aprotic polar solvent is used usually in an amount within a range of from 100 to 1000 g, preferably from 150 to 500 g, per mol of the halogenated benzoate of the formula II.

This reaction is conducted usually at a temperature within a range of from 150° to 300° C., preferably from 160° to 200° C. There is no particular restriction as to the reaction pressure, and the reaction may be conducted under atmospheric pressure or under positive pressure. When the reaction is conducted under positive pressure, the pressure is preferably at most 10 kg/cm². From the industrial point of view, the reaction is preferably to the aromatic ring decarboxylation and formation of high boiling substances and to produce a fluorobenzoate of the formula I in an industrially feasible manner. Further, the fluorobenzoate obtained by this method is useful as an intermediate for the production of fluorophenyl isocyanate.

Now, the present invention will be described in further detail with reference to Examples. However, it should be understood that the present invention is by no means restricted by such specific Examples.

EXAMPLE 1

Into a 50 ml three-necked flask equipped with a condenser and a stirrer, 6.0 g (104 mmol) of spray-dried potassium fluoride (purchased from Morita Kagaku Kogyo K.K.), 1.7 g (4 mmol) of tetraphenyl phosphonium bromide, 12 g of anhydrous sulfolane and 20 ml of toluene, and the mixture was heated and stirred in an oil bath to distill off toluene and to conduct azeotropic removal of water. The mixture was heated at 140° C., and then the pressure was reduced to a level of 45 mmHg to distill off substantially all the remaining toluene. The content of the flask was cooled to 100° C. and substituted by nitrogen gas. Then, 13.1 g (40 mmol) of neopentyl 2,3,4,5-tetrachlorobenzoate was added thereto, and the mixture was reacted under a nitrogen gas atmosphere at 190° C. under stirring for 15 hours.

After completion of the reaction, the reaction mixture was cooled and after an addition of 100 ml of toluene, subjected to filtration to remove inorganic substances. The filtrate was washed three times with 200 ml of water. The toluene layer was dried over anhydrous sodium sulfate, and concentrated under reduced pressure by a rotary evaporator to obtain 11.0 g of a brown oily substance. The oily substance thus obtained was distilled under reduced pressure to obtain 7.2 g of neopentyl 3,5-dichloro-2,4-difluorobenzoate as a colorless oil. The yield was 61%. The analytical data of the infrared spectrum (hereinafter referred to simply as IR), the nuclear magnetic resonance spectrum (hereinafter referred to simply as NMR) and the mass spectrum (hereinafter referred to simply as Mass) of this compound are shown below.

Boiling point: 115°–117° C./2 mmHg
Melting point: 38°–42° C.
IR (KBr): 1720(C=O), 1250(C-F)cm$^{-1}$
$^1$H-NMR δ (CDCl$_3$): 7.93(dd,J=8.0Hz,8.0Hz,1H), 4.07(s,2H), 1.07(s,9H)
Mass m/e: 296(M$^+$), 209(M$^+$—CH$_2$C)CH$_3$)$_3$)

EXAMPLE 2

The reaction was conducted in the same manner as in Example 1 for 6 hours by using 8.9 g (30 mmol) of neopentyl 3,4,5-trichlorobenzoate instead of neopentyl 2,3,4,5-tetrachlorobenzoate in Example 1, 2.6 g (45 mmol) of spray-dried potassium fluoride, 1.3 g (3 mmol) of tetraphenyl phosphonium bromide and 9 g of anhydrous sulfolane. The post-treatment was conducted in the same manner, followed by distillation under reduced pressure to obtain 5.3 g of neopentyl 3,5-dichloro-4-fluorobenzoate. Further, the distillation residue was subjected to silica gel column chromatography and eluted with benzene to obtain 2.0 g of neopentyl 3,5-dichloro-4-fluorobenzoate as slightly yellow plates. The combined yield was 87%. The physical properties are shown below.

Boiling point: 137°–140° C./7 mmHg
Melting point: 96°–98° C.
IR (KBr): 1730(C=O), 1240(C-F)cm$^{-1}$
$^1$H-NMR δ (CDCl$_3$): 7.85(d,J=6.0Hz,2H), 3.97(s,2H) 1.03(s,9H)
Mass m/e: 278(M$^+$), 191(M$^+$—CH$_2$C(CH$_3$)$_3$)

EXAMPLE 3

The reaction and post-treatment were conducted in the same manner as in Example 1 except that 9.9 g (30 mmol) of neopentyl 2,3,4,5-tetrachlorobenzoate, 4.0 g (69 mmol) of spray-dried potassium fluoride and 9 g of sulfolane were employed, and instead of tetraphenyl phosphonium bromide in Example 1, 0.8 g (3 mmol) of N-(2-ethylhexyl)-4-dimethylaminopyridinium chloride was used, whereby 5.7 g of 3,5-dichloro-2,4-difluorobenzoate was obtained. The yield was 64%.

EXAMPLE 4

The operation was conducted in the same manner as in Example 2 except that 0.8 g (3 mmol) of N-(2-ethylhexyl)-4-dimethylaminopyridinium chloride was used instead of tetraphenyl phosphonium bromide in Example 2, whereby 7.6 g of neopentyl 3,5-dichloro-4-fluorobenzoate was obtained. The yield was 91%.

EXAMPLE 5

Into a three-necked 50 ml flask equipped with a condenser and a stirrer, 1.9 g (33 mmol) of spray-dried potassium fluoride (purchased from Laporte Industry), 1.1 g (2.5 mmol) of tetraphenyl phosphonium bromide, 0.7 g (2.5 mmol) of 18-crown-6 and 6.4 g (25 mmol) of ethyl 3,4,5-trichlorobenzoate were introduced, and the mixture was heated in an oil bath and reacted under a nitrogen atmosphere at 210° C. for 2 hours. The reactor was cooled, and the mixture was diluted with 40 ml of toluene. Inorganic salts were filtered off, and toluene was concentrated to give the residue, which was distilled under reduced pressure to obtain 3.4 g of ethyl 3,5-dichloro-4-fluorobenzoate. The yield was 57%. The physical properties are shown below.

Boiling point: 109°–115° C./5 mmHg
Mass m/e: 236(M+), 208(M+—CH$_2$=CH$_2$)

I claim:

1. A process for producing a fluorobenzoate having the formula

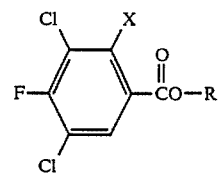

wherein X is a fluorine atom or a hydrogen atom, and R is an alkyl group, which comprises reacting a chlorobenzoate having the formula:

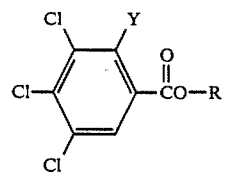

wherein Y is a hydrogen atom or a chlorine atom, and R is as defined above, with a metal fluoride.

2. The process according to claim 1, wherein the reaction is conducted in an aprotic polar solvent in the presence of at least one salt selected from the group consisting of quaternary phosphonium salts, quaternary ammonium salts and pyridinium salts, as catalyst.

3. The process according to claim 1, wherein the reaction is conducted in the presence of a combination of at least one salt selected from the group consisting of quaternary phosphonium salts, quaternary ammonium salts and pyridinium salts, and at least one compound selected from the group consisting of crown ethers and polyalkylene glycols, as catalyst.

* * * * *